United States Patent
Dullea et al.

(10) Patent No.: US 7,651,988 B2
(45) Date of Patent: Jan. 26, 2010

(54) CLEANSER COMPOSITIONS COMPRISING A GASIFIED CANDY AS A SENSORY SIGNAL

(75) Inventors: Charles V. Dullea, Parsippany, NJ (US); Stanley J. Lech, Parsippany, NJ (US); Naresh I. Mehta, Parsippany, NJ (US); Stuart Wilensky, Parsippany, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 765 days.

(21) Appl. No.: 10/582,042

(22) PCT Filed: Dec. 15, 2004

(86) PCT No.: PCT/US2004/041956

§ 371 (c)(1), (2), (4) Date: Jun. 7, 2006

(87) PCT Pub. No.: WO2006/065239

PCT Pub. Date: Jun. 22, 2006

(65) Prior Publication Data

US 2007/0054830 A1    Mar. 8, 2007

Related U.S. Application Data

(60) Provisional application No. 60/529,521, filed on Dec. 15, 2003.

(51) Int. Cl.
*C11D 13/18* (2006.01)
*C11D 3/3951* (2006.01)

(52) U.S. Cl. .................. 510/117; 510/116; 510/146; 510/438

(58) Field of Classification Search .......... 510/116, 510/117, 146, 438
See application file for complete search history.

(56) References Cited

U.S. PATENT DOCUMENTS

| | | | |
|---|---|---|---|
| 4,155,868 A | 5/1979 | Kaplan et al. ............. 252/95 |
| 4,263,328 A | 4/1981 | Parada et al. ............ 426/103 |
| 4,568,534 A | 2/1986 | Stier et al. | |
| 4,876,082 A | 10/1989 | Romeo | |
| 5,055,305 A | 10/1991 | Young ..................... 424/466 |
| 5,571,519 A * | 11/1996 | Synodis et al. ........... 424/405 |
| 5,786,316 A * | 7/1998 | Baeck et al. ............ 510/235 |
| 6,077,501 A * | 6/2000 | Sickora et al. ............ 424/49 |
| 6,083,488 A * | 7/2000 | Riccobono et al. ........ 424/44 |
| 6,235,318 B1 | 5/2001 | Lombardy, Jr. et al. | |
| 6,254,857 B1 | 7/2001 | Hoic et al. | |
| 6,310,014 B1 | 10/2001 | Rau | |
| 6,488,961 B1 * | 12/2002 | Robinson et al. ......... 424/466 |
| 6,491,896 B1 * | 12/2002 | Rajaiah et al. ............ 424/44 |
| 2003/0078179 A1 * | 4/2003 | Ghosh et al. ............ 510/392 |

FOREIGN PATENT DOCUMENTS

| EP | 0298839 A1 | 1/1989 |
|---|---|---|
| EP | 1059076 A2 | 12/2000 |
| JP | 02121917 | 5/1990 |
| WO | WO02/098240 | 12/2002 |

OTHER PUBLICATIONS

Derwent Publications, Ltd., AN1900509-188380: XP002453209.

* cited by examiner

*Primary Examiner*—Charles I Boyer
(74) *Attorney, Agent, or Firm*—Nora Stein-Fernandez; Theodore R. Furman

(57) ABSTRACT

A cleanser composition suitable for use with oral appliances, which provides a sensory signal to the user. The sensory signal is such that the user believes the signal to indicate that cleansing of the oral device if occurring or, alternatively, that cleansing action has ceased.

7 Claims, No Drawings

US 7,651,988 B2

CLEANSER COMPOSITIONS COMPRISING A GASIFIED CANDY AS A SENSORY SIGNAL

This application is a 371 of International Application No. PCT/US2004/041956, filed Sep. 15, 2004, which claims the benefit of U.S. Provisional Application No. 60/529,521, filed Dec. 15, 2003.

FIELD OF THE INVENTION

The present invention relates to a cleanser composition that is suitable for use with oral appliances and which provides a sensory signal to the consumer upon use.

BACKGROUND OF THE INVENTION

Like teeth, dentures, partials, retainers, oral devices and even toothbrushes should be cleaned regularly to maintain good oral health and for cosmetic purposes. Of course, unlike teeth, these appliances can be removed from the oral cavity for cleaning.

For instance, dentures and partials (hereinafter, collectively, "dentures") are typically cleaned in one of two ways: either the dentures, once removed from the oral cavity, are brushed with dentifrices or specially formulated cleansing creams; or dentures are soaked for some time in a cleansing bath.

Brushing of the denture is similar to brushing of the natural teeth in that, a cream cleanser is applied to a dental brush, such as a toothbrush, and brushing of the denture to remove plaque, adhesive residue and debris follows. The cleansing routine is quick and no more cumbersome than the brushing of natural teeth and denture wearers are likely to partake of the practice.

Alternatively, the denture or device may be cleaned by submersion into a cleansing bath. Full immersion of the device in the bath allows the cleansing composition to reach all areas of the device or denture. Typically, a powder or tablet comprising the cleansing agents is dissolved in water to form a cleansing bath. Such formulations generally contain an effervescent system and strong chemical cleaning agents to supplement or altogether replace the need for brushing of the denture or device.

To encourage the use of denture and oral device cleansers, thereby promoting healthy remaining natural teeth and gums, recent developments have focused on improving speed of cleansing to increase user compliance with a cleansing regimen. To that end, cleansers, such as denture cleanser baths, have been produced, that work within five minutes or less to sufficiently clean the denture. However, not all denture and oral device wearers may be aware of these significant advances in speed of cleansing.

Thus, in an effort to educate consumers as to the fast cleansing action and to further improve compliance with a cleansing regimen for all oral devices, the present invention provides the consumer with a signal upon use. The consumer may perceive the signal as indicating that the cleanser is working or, alternatively that the cleanser has completed its disinfecting and cleansing action. More particularly, the present invention relates to cleansers, suitable for use on oral appliances, wherein said cleansers provide a sensory signal to the consumer.

SUMMARY OF THE INVENTION

The present invention relates to a cleanser composition suitable for oral appliances, such as dentures, partials, retainers, toothbrushes and the like, comprising an agent that provides a sensory signal to the user. The sensory signal is such that the user believes the signal to indicate that cleansing of the oral device is occurring. Alternatively, the sensory signal may indicate to the consumer that the cleansing action is complete. In one embodiment, a powder or tablet comprising cleansing agents produces an audible signal upon the powder or tablet coming into contact with water. The audible signal may continue for a predetermined period of time, such as 10 minutes or less. In one embodiment, termination of the audible signal is timed so that adequate time has passed to achieve sufficient cleaning of the oral device prior to said termination.

DETAILED DESCRIPTION OF THE INVENTION

The present invention relates to a cleanser composition suitable for disinfecting oral appliances comprising a sensory signal to the consumer. For purposes herein, the term "oral appliance" is meant to include any device that is suitable for prolonged, temporary or intermittent use in the oral cavity, such as dentures, partials, retainers, toothbrushes and the like, and which can be removed from the oral cavity for cleaning.

The sensory signal to be incorporated in the cleansing compositions of the present invention may be any sensory signal that would be received by the cleanser user, such as a visual, audible, or aromatic signal. The sensory signal must be of sufficient intensity and duration that the consumer is conscious of the signal while using the cleansing composition. The sensory signal may commence at any time that the cleanser composition is in use. For example, the signal may be emitted immediately, such as when the composition is introduced to an aqueous environment. Or the signal may commence once sufficient time has passed for adequate cleansing to be achieved. In one embodiment the signal is such that the user perceives the commencement of the signal to indicate that cleansing of the oral appliance has begun and, upon cessation of the signal, that cleansing of the oral appliance has ceased. The sensory signal may be an audible signal of adequate volume and duration to be heard by the consumer utilizing the cleansing composition and which the consumer perceives as indicating that the composition is working and which ceases when adequate time has elapsed for sufficient cleansing action to occur. The cleansing composition may be a powder or tablet comprising a cleansing component suitable for use with oral appliances, which produces an audible signal upon the powder or tablet coming into contact with water. The audible signal may continue for a predetermined period of time, such as 10 minutes or less. In one embodiment, the length of audible signal is timed to coincide with the period of time necessary for the cleanser composition to provide sufficient disinfection and cleansing of the oral appliance, such as 5 minutes, 3 minutes or 1 minute.

In another embodiment, the sensory signal may be timed so as to commence after sufficient time has passed for adequate cleansing to have occurred and to be perceived by the consumer as indicating that the cleansing period is completed.

The length of the audible signal may be manipulated by various means. For example, the audible signal may be triggered by the presence of a certain cleansing component, which may be consumed during the disinfection of the oral appliance. Once the cleansing component is consumed, the audible signal ceases.

Alternatively, the audible signal may provided by the incorporation of a gasified material to the cleanser component, in sufficient quantities to maintain the audible signal for at least 10 minutes, in one embodiment for at least 5 minutes, in another embodiment for at least 3 minutes and in yet another embodiment for at least 1 minute.

In one embodiment, the compositions of the present invention are achieved by the addition of a suitable gasified material, to serve as the sensory signal component, to a standard denture or oral appliance cleanser. Suitable gasified materials include but are not limited to a gasified candy that is formulated to produce a very pronounced popping sound. Examples of such candies include POP ROCKS®, which are commercially available and marketed by Zeta Espacial S.A., distributed by Pop Rocks, Inc., Falls Church, Va. POP ROCKS® are more particularly described in U.S. Pat. No. 4,289,794 to Kleiner et al., incorporated herein by reference.

Where a gasified candy is incorporated in the compositions of the present invention to provide an audible sensory signal, the candy may be a hard sugar product having bubbles of gas entrapped therein and provided in granulated form. The gasified candy can be prepared from any commercially available sugars known in the confectionery arts. Thus, sugars such as glucose, fructose, sucrose, lactose, and the like, either alone or in combination, may be employed. A mixture of one or more sugars in combination with corn syrup may also serve as a satisfactory base for the gasified candy. Alternatively, a sugarless form of gasified candy may be employed in the compositions of the present invention. Where a sugarless gasified candy is preferred, a sugar substitute, such as sorbitol or aspartame may be substituted for the sugar component.

The gasses used to prepare the gasified candy may be any of the commercially available gases that are substantially unreactive with the sugar or sugars being employed, such as carbon dioxide, nitrogen or air. The gasified candy contains from about 0.5 to about 15 $cm^3$ of gas per gram of candy. The moisture content of the gasified material is typically between about 1% to about 5%.

Gasified candy may be manufactured by those processes known in the art and as more particularly described in U.S. Pat. Nos. 3,012,893 to Kremzner et al.; 3,985,910 and 3,895,910 to Kirkpatrick; 4,001,457 to Hegadorn; 4,289,794 to Kleiner et al.; 4,837,039, 4,952,417 and 5,165,951 all to Gallart et al.

The cleansing compositions of the present invention also comprise a cleanser component in addition to a sensory signal. The cleansing component can be any cleanser suitable for use on oral appliances. For example, dentifrices, particularly those in powder form; denture cleansers including, but not limited to, those denture cleansers sold as POLIDENT® by GlaxoSmithKline d/b/a Smithkline Beecham Corporation and as FIXODENT® by The Procter & Gamble Company; toothbrush cleansers, such as AQUABLAST® sold by GlaxoSmithKline d/b/a Smithkline Beecham Corporation; and any other cleanser for use on oral appliances are suitable for use in the cleanser compositions of the present invention.

Such cleansers are typically formulated with effervescent systems and one or more bleaching agents, and may contain one or more of any of the following; surfactants builders and chelating agents; flavorants, colorants; foam stabilizers; buffering agents; excipients; and, optionally, enzymes to remove unsightly stains and debris from the oral appliance.

Bleaching agents, typically take the form of an inorganic persalt and can be selected from any of the well-known bleaching agents known for use in oral care and denture care compositions such as the alkali metal and ammonium persulfates, perborates, percarbonates, peroxycarbonates and perphosphates and the alkali metal and alkaline earth metal and organic acid peroxides. Examples of suitable bleaching agents include potassium, ammonium, sodium and lithium persulfates and perborate mono- and tetrahydrates, sodium pyrophosphate peroxyhydrate and magnesium, calcium, strontium and zinc peroxides. Suitable bleaching agents also include chlorine or hypochlorite generating materials, such as heteroxcyclic n-chloroimides, for example, sodium chloroisocyanurate chlorinated hydantoins, such as 1,3-dichloro-5,5-dimethylhydantoin, and, for example, Dactin®, and dry inorganic compounds such as calcium and sodium hypochlorite. The bleaching agent component is preferably present in the tablet in an amount within the range of about 1% to about 80%, based upon total cleanser component weight, and in one embodiment in an amount within the range of about 5% to about 55%.

The cleansing component may also comprise an effervescence system that takes the form of a solid base material that, in the presence of water, releases carbon dioxide or oxygen with effervescence. In general, the effervescent system contained within the cleanser component does not produce a sensory signal of sufficient intensity and duration to signify to the consumer that cleansing has begun and thereafter, when the effervescence generator is consumed, has ceased. Suitable effervescent systems, based on aqueous reactions, include: alkali metal carbonates or alkali metal persulfates with carboxylic acids; and alkali metal hydrogen carbonates in combination with carboxylic acids, such as citric acid or acid anhydrides; reactions of organic chlorine materials, such as heterocyclic N-chloroimides with peroxygen agents, such as alkali metal salts of perborate or peroxycarbonate; and other known carbon dioxide and/or oxygen liberating reactions common to compositions in this art.

Suitable surfactants for use in the cleanser compositions herein include: anionics such as carboxylic acid salts, for example, sodium salts of straight chain fatty acids; sulfonic acid salts, such as linear alkylbenzene sulfonates ($C_{13}$-$C_{15}$), petroleum sulfonates, secondary n-alkanesulfonates, sulfosuccinate esters, sulfated linear primary alcohols ($C_{12}$-$C_{20}$), sulfated polyoxyethylenated straight chain alcohols, sulfated triglycerides; nonionics, such as polyoxyethylenated alkyl phenols, polyoxyethylenated mercaptans, long chain carboxylic acid esters, polyoxyethylenated straight-chain alcohols, alkanolamine condensates, N-alkylbetaines, N-alkyl-.beta.-iminodipropionic acids, imidazoline carboxylates and sulfo-betaines; cationics; such as long chain amine hydrochlorides and polyoxyethylenated long chain amine hydrochlorides, for example, salts of primary amines derived from vegetable and animal fatty acids, tall oil or synthetic $C_{12}$-$C_{18}$ primary, secondary and tertiary amines, diamines and polyamines.

The cleansing component comprises an effective amount of builders and sequestering/chelating agents to clean the desired oral appliance. In one embodiment, the amount of sequestering/chelating agent should be sufficient to cleanse the oral appliance in a moderate volume of water. Suitable builders and chelating agents include: complex phosphates, such as sodium tripolyphosphate, sodium hexametaphosphate; alkali metal carbonates; alkali metal silicates; zeolites; and salts of carboxylic acids, such as sodium citrate; alkali metal salts of ethylenediamine tetraacetic acid; polymeric salts; and acrylic and maleic acids and their copolymers. A mixture of sequestering/chelating agents may be suitable for use in the present compositions. For example, hexametaphosphate and ethylenediamine tetraacetic acid (EDTA) may comprise a sequestering/chelating system.

Suitable excipients for use herein include: binding compounds, such as polyvinyl-pyrrolidone and polyethylene glycols; lubricants, such as fumed silicas and alkali metal salts of saturated fatty acids; fillers, such as sodium sulfate, alkali metal acid carbonates and carbonates.

Suitable buffering systems for use in the cleanser component include: combinations of neutralized and free alkali metal carbonates, silicates, phosphates, carboxylic acids, and other ionizable species that influence the concentration of (H+), (OH—).

The cleanser component may be formulated to be enzymatic, if desired. Any suitable enzyme material, such as those derived from various strains of *Bacillus subtilis* (also known as subtilisins) and *Bacillus licheniformis*, such as those sold under the trademarks Durazym, Esperase, Savinase, Maxatase, Alcalase, Everlase and Endodextranase may be utilized in the composition. Where the final composition is in the form of a tablet, the enzyme should be separated from any flavorant to avoid degradation of the enzyme prior to use. This can be done through any means known in the art such as encapsulation, separation through layering of the tablet, etc.

Colorants and flavorants may be incorporated into the compositions of the present invention to enhance the visual and appeal of the cleanser composition and to provide a pleasant taste to the consumer. These colorants and flavorants, where present, may be added to the sensory signal component, the cleansing component, or both. Preferred flavorants for use in the compositions of the present invention are the natural mint oils peppermint and spearmint, but other flavorants such as menthol, oil of wintergreen, and citrus flavors, such as lemon, lime and orange, may also be used. Other suitable flavorants and flavor oils will be apparent to one skilled in the art. The flavoring component is preferably present in the tablet in an amount within the range of about 0.05% to about 4.0% based upon the total composition weight, and most preferably in an amount within the range of about 0.1% to about 2%. Commercial colorants are available in a variety of hues and the choice of color will depend on the desired effect. One of skill in the art will be able to determine which colorant and at what levels are appropriate for use in the present compositions.

The cleanser component of the present invention may be in any form useful for carrying out the purpose, i.e., aqueous solution, liquid concentrate, powder, tablet or other solid system. In one embodiment, the cleanser component is a granulate in tablet or powder form. Where the sensory signal is an audible signal produced by a gasified material, the final composition is typically a granulate in tablet or powder form that is substantially water soluble. In order to begin the cleansing action and the accompanying sensory signal, the consumer will introduce sufficient water to the tablet for the tablet to readily disintegrate, for example, by dropping the tablet into a glass containing 8 ounces of room temperature or warm water and the oral appliance to be cleaned.

The invention will now be illustrated in greater detail with reference to the following examples, but it should be understood that these are not intended to limit the present invention.

Examples

| All Amounts Reported in Weight %. | | | | | |
|---|---|---|---|---|---|
| Ingredient | Ex. A | Ex. B | Ex. C | Ex. D | Ex. E |
| Sodium Bicarbonate #1 | 34.425 | 33.432 | 38.425 | 34.55 | 38.55 |
| Sodium Carbonate, Anhydrous | 11 | 11 | 11 | 11 | 11 |
| Flavor | 2 | 2 | 2 | 2 | 2 |
| Citric Acid | 21.5 | 20.288 | 21.5 | 23.475 | 23.475 |

-continued

| All Amounts Reported in Weight %. | | | | | |
|---|---|---|---|---|---|
| Ingredient | Ex. A | Ex. B | Ex. C | Ex. D | Ex. E |
| Potassium Monopersulfate | 4 | 4 | 4 | | |
| Sodium Perborate, Monohydrate | 12 | 12 | 12 | 13.4 | 13.4 |
| Sodium Lauryl Sulfate | | 4 | | 3 | 3 |
| Sodium Lauryl Sulfoacetate | 3 | | 3 | | |
| Gasified candy* | 9 | 10 | 5 | 9 | 5 |
| Sodium Polyphosphate | 3 | 3 | 3 | 3 | 3 |
| Fumed Silica | | | | 0.5 | 0.5 |
| Dye (Lake) | 0.05 | 0.14 | 0.05 | 0.05 | 0.05 |
| Dye (soluble) | 0.025 | 0.14 | 0.025 | 0.025 | 0.025 |
| Total | 100 | 100 | 100 | 100 | 100 |

*Particle size between 0.01-12 mm

The above formulations are prepared by initially combining the sodium bicarbonate and the sodium carbonate components into a tote bin under dehumidified conditions. A mixer, such as a Hobart mixer, manufactured by Hobart Corporation, Troy, Ohio is used to blend the components for about three minutes. Flavor is added and mixing continues for an about three more minutes. Citric acid is then added and mixing continues for one minute. Potassium monopersulfate is added to the mixture and mixing continues for about one minute. Sodium perborate is then added to the mixture and mixing continues for about one minute. Sodium lauryl sulfate is next added and mixing continued for about one minute. Sodium lauryl sulfoacetate is added and mixing continues for about one more minute. The gasified candy is added and mixing continues for about one minute. Sodium polyphophate is added and mixing for about three minutes follows. Where fumed silica is utilized, it is next added and mixing ensues for about three minutes. Colorants, such as the dyes, are then added separately and with mixing for about three minutes following each addition. The resulting granulation may be utilized in powder form or may be tabletted for use by any means known in the art.

All publications, including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration it is believed that one skilled in the art can, given the preceding description, utilize the present invention to its fullest extent. Therefore any examples are to be construed as merely illustrative and not a limitation on the scope of the present invention in any way. The embodiments of the invention in which an exclusive property or privilege is claimed are defined as follows.

What is claimed is:

1. An oral appliance cleanser composition comprising:
   a) a cleansing component comprising:
      i) a bleaching agent,
      ii) a surfactant,
      iii) a sequestering/chelating agent selected from the group consisting of sodium polyphosphate and ethylenediamine tetraacetic acid, and b) a sensory signal component providing a sensory signal of sufficient intensity and duration that the consumer perceives the sensory signal to indicate the commencement or cessation of the cleansing action, wherein the sensory signal component is a gasified candy comprising:
   i) at least one sugar selected from the group consisting of glucose, fructose, sucrose and lactose,
   ii) corn syrup,
   iii) optionally a sugar substitute, and
   iv) a gas that is unreactive with the sugar or sugar substitute.

2. The oral appliance cleanser composition of claim 1 wherein the sensory signal is an audible signal.

3. The cleanser composition of claim 1 wherein the bleaching agent is selected from the group consisting of the alkali metal and ammonium persulfates, perborates, percarbonates, peroxycarbonates and perphosphates and the alkali metal and alkaline earth metal and organic acid peroxides.

4. The cleanser composition of claim 1 wherein the cleansing component further comprises at least one effervescent system, binder, flavorant, colorant, tabletting agent, enzyme, foam stabilizing agent, lubricant, buffering system, or mixtures thereof.

5. The cleanser composition of claim 4 wherein the effervescent system comprises sodium bicarbonate and citric acid.

6. The cleanser composition of claim 4 formulated and compressed as a tablet.

7. The cleanser composition of claim 1 wherein the surfactant is selected from the group consisting of sodium lauryl sulfate, sodium lauryl sulfoacetate, disodium N-alkyl sulfosuccinate, disodium lauryl sulfosuccinate, sodium olcyl sulfate, and mixtures thereof.

* * * * *